(12) United States Patent
Msika et al.

(10) Patent No.: US 8,877,261 B2
(45) Date of Patent: Nov. 4, 2014

(54) ANTI-REDNESS ACTIVE AGENT AND COSMETIC COMPOSITIONS COMPRISING SAME

(75) Inventors: Philippe Msika, Versailles (FR); Caroline Baudouin, Rambouillet (FR); Franck Menu, Sorel Moussel (FR)

(73) Assignee: Laboratoires Expanscience, Courbevoie (FR)

( * ) Notice: Subject to any disclaimer, the term of this patent is extended or adjusted under 35 U.S.C. 154(b) by 0 days.

(21) Appl. No.: 13/824,699

(22) PCT Filed: May 11, 2012

(86) PCT No.: PCT/EP2012/058798
§ 371 (c)(1),
(2), (4) Date: Mar. 18, 2013

(87) PCT Pub. No.: WO2012/156319
PCT Pub. Date: Nov. 22, 2012

(65) Prior Publication Data
US 2013/0177662 A1 Jul. 11, 2013

(30) Foreign Application Priority Data
May 13, 2011 (FR) .................................. 11 54181

(51) Int. Cl.
| | |
|---|---|
| A61K 36/00 | (2006.01) |
| A61K 31/74 | (2006.01) |
| A61K 8/97 | (2006.01) |
| A61K 36/48 | (2006.01) |
| A61K 8/64 | (2006.01) |
| A61K 8/34 | (2006.01) |
| A61K 8/73 | (2006.01) |
| A61Q 19/00 | (2006.01) |
| A61Q 19/10 | (2006.01) |
| A61K 38/16 | (2006.01) |
| A61Q 19/08 | (2006.01) |
| A61Q 17/04 | (2006.01) |

(52) U.S. Cl.
CPC . *A61K 8/73* (2013.01); *A61K 36/48* (2013.01); *A61Q 19/007* (2013.01); *A61Q 19/10* (2013.01); *A61K 8/645* (2013.01); *A61K 38/168* (2013.01); *A61Q 19/08* (2013.01); *A61K 8/347* (2013.01); *A61Q 17/04* (2013.01); *A61Q 19/00* (2013.01)
USPC .......................... 424/725; 424/78.05; 514/1.1

(58) Field of Classification Search
None
See application file for complete search history.

(56) References Cited

U.S. PATENT DOCUMENTS

| | | | | |
|---|---|---|---|---|
| 7,029,713 B2 * | 4/2006 | Msika et al. | ................... | 424/776 |
| 2009/0264341 A1 * | 10/2009 | Arora et al. | ....................... | 514/8 |

FOREIGN PATENT DOCUMENTS

| | | |
|---|---|---|
| FR | 2855050 A1 | 11/2004 |
| FR | 2885301 A1 | 11/2006 |
| WO | WO-00/62789 A1 | 10/2000 |
| WO | WO-2010/052327 A1 | 5/2010 |

OTHER PUBLICATIONS

Bevins et al., "Rosacea: skin innate immunity gone awry?", Nature Medicine, vol. 13, No. 8, Aug. 2007, pp. 904-906.
French Preliminary Search Report issued for Application No. FR 1154181, dated Jan. 16, 2012, 2 pages.
Gomaa et al., "Lymphangiogenesis and angiogenesis in non-phymatous rosacea", Journal of Cutaneous Pathology, vol. 34, 2007, pp. 748-753.
Guzman-Sanchez et al., "Enhanced skin blood flow and sensitivity to noxious heat stimuli in papulopustular rosacea", J Am Acad Dermatol, vol. 57, 2007, pp. 800-805.
International Search Report issued for Application No. PCT/EP2012/058798 dated May 11, 2012, 4 pages.
Koczulla et al., "An angiogenic role for the human peptide antibiotic LL-37/hCAP-18", The Journal of Clinical Investigation, vol. 111, No. 11, Jun. 2003, pp. 1665-1672.
Laquer et al., "Angiogenesis in cutaneous disease: Part II", J Am Acad Dermatol, vol. 61, 2009, pp. 945-958.
Rodriguez-Martinez et al., "LL-37 regulates the overexpression of vascular endothelial growth factor (VEGF) and c-IAP-2 in human keratinocytes", International Journal of Dermatology, vol. 47, 2008, pp. 457-462.
Smith et al., "Expression of vascular endothelial growth factor and its receptors in rosacea", Br J Ophthalmol, vol. 91, 2007, pp. 226-229.
Stetler-Stevenson, "Matrix metalloproteinases in angiogenesis: a moving target for therapeutic intervention", The Journal of Clinical Investigation, vol. 103, No. 9, May 1999, pp. 1237-1241.
Tokumaru et al., "Induction of Keratinocyte Migration via Transactivation of the Epidermal Growth Factor Receptor by the Antimocrobial Peptide LL-37", The Journal of Immunology, vol. 175, 2005, pp. 4662-4668.
Yamasaki et al., "Increased serine protease activity and cathelicidin promotes skin inflammation in rosacea", Nature Medicine, vol. 13, No. 8, Aug. 2007, pp. 975-980.
Yamasaki et al., "Kallikrein-mediated proteolysis regulates the antimicrobial effects of cathelicidins in skin", FASEB Journal, vol. 20, 2006, pp. 2068-2080.
Yamasaki et al., "The molecular pathology of rosacea", J Dermatol Sci, vol. 55, No. 2, Aug. 2009, pp. 77-81.
Yamasaki et al., "TLR2 Expression Is Increased in Rosacea and Stimulates Enhanced Serine Protease Production by Keratinocytes", J Invest Dermatol., vol. 131, No. 3, Mar. 2011, pp. 688-697.

* cited by examiner

*Primary Examiner* — Chris R Tate
*Assistant Examiner* — Deborah Davis
(74) *Attorney, Agent, or Firm* — Foley & Lardner LLP (57) ABSTRACT

The present application relates to a cosmetic method for preventing and/or treating skin redness, characterized in that a composition comprising arabinogalactan is administered to a person who may form or who is displaying redness. This cosmetic composition can be administered topically or orally.

9 Claims, 2 Drawing Sheets

ANTI-REDNESS ACTIVE AGENT AND COSMETIC COMPOSITIONS COMPRISING SAME

The present invention relates to the prevention and treatment of skin redness, often considered unsightly. It relates to the use of arabinogalactan and to cosmetic compositions comprising same, for the prevention and treatment of redness, in a cosmetic method. One particularly effective composition against skin redness comprises arabinogalactan and lupin peptides. A cosmetic method for preventing and/or treating skin redness, comprising the administration of a composition comprising arabinogalactan to a person prone to cutaneous redness, is provided.

INTRODUCTION

Skin redness is a skin disorder, primarily present on the face, which can have various origins. It may be of short duration (flushes) or may be permanent. Secondary criteria may appear as a burning sensation, tingling, red blotches, dry skin or facial edema. Depending on the severity of this redness, the esthetic price may be very high and accompanied by disastrous social consequences. It is estimated that 10% of Europeans are concerned.

People with cutaneous redness generally have skin that is abnormally sensitive to the environment, and to numerous factors such as hot beverages, alcohol, temperature changes, spicy foods, exercise, stress and strong emotions, sunlight, etc.

How this redness appears is poorly understood and multifactorial: it involves genetic, inflammatory and vascular factors.

Recently, Dr. Gallo's team [1] discovered and demonstrated the involvement of an altered innate immune response in the initiation of skin disorders, and proposes various molecular mechanisms and interconnected key elements in the appearance of redness: 1) altered innate immunity; 2) vascular disorders; 3) microbes; 4) oxidative stress and sun.

1—Dysregulation of the Innate Immune Response

The innate immune system involves a recognition system including Toll-like receptors (TLRs) capable of responding to many environmental stimuli such as UV, microbes and physical and chemical trauma. Following the recognition stage, the innate immune response is initiated with a controlled production of mediators such as cytokines and antimicrobial peptides (AMPs). Among AMPs, cathelicidins LL37 have antimicrobial properties, but are also involved in healing and in initiation of the acquired immune response by properties of chemotaxis. To release the active form of cathelicidin LL37, the pro-form must be cleaved by a serine protease enzyme called kallikrein-5 or stratum corneum tryptic enzyme (SCTE).

In biopsies of patients presenting rednesses (notably due to dilation of the superficial blood vessels on the surface of the skin), the quantity of cathelicidins LL37 is strongly increased. In comparison with normal skin, cathelicidins LL37 are not only present in greater quantity but have a different peptide profile; consequently, these cathelicidins are called "LL37 variants." These LL37 variants exhibit vasoactive and proinflammatory properties by inducing the production of IL-8 and certain proangiogenic mediators [2, 3]. The presence of these LL37 variants in a large quantity in skin prone to redness is explained by an abnormal production of the protease kallikrein-5, which matures the pro-forms of LL37 into active forms [4]. These kallikrein proteases are also capable of breaking down corneodesmosomes and are thus involved in desquamation. They are also capable of digesting elements of the extracellular matrix (ECM) such as collagens type I, II, III and IV, fibronectin and laminin. Thus, considering that KLK5 production is increased in certain skin disorders, these proteases may play an important part in the associated inflammatory reactions and affect the dermal and vascular matrix.

All of this was confirmed experimentally by the injection of peptides LL37 or enzyme KLK5 into the skin of mice, inducing cutaneous inflammation (erythema, vasodilatation) that mimics the changes observed in erythrocouperosis [5].

The same team has just shown that the expression of TLR2 is abnormally high [6], this increasing the susceptibility to certain stimuli and leading to an increased production of kallikreins and cathelicidins and thus to an exacerbated response that the same stimuli would not have induced in normal subjects.

Figure 1:
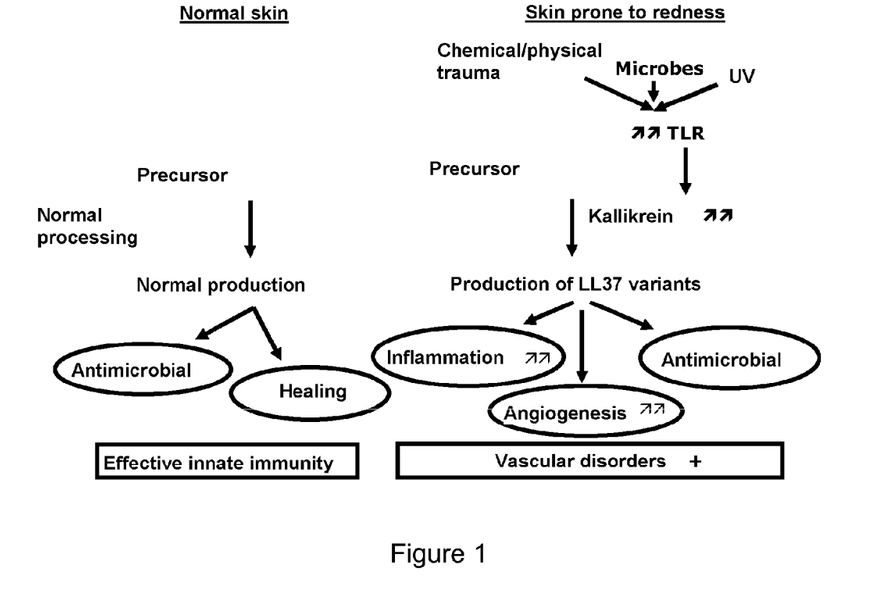
FIG. 1: Key role of innate immunity in an outbreak of redness in people prone to redness, in relation to those with normal skin; review by Bevins C L and Liu T F [7].

FIG. 1 illustrates the involvement of the innate immune response.

2—Vascular Disorders

Many people experience episodes of "flushes"; this leads to the hypothesis of a vascular hyper-reactivity playing a large role in this unsightly phenomenon. Some studies show an increase in blood flow in the cutaneous lesions of patients presenting with skin redness [8]. The factors triggering these flushes, such as emotional stress, spicy foods, hot beverages, high ambient temperatures and menopause, aggravate an outbreak of redness and support the vascular theory [8].

Erythrocouperosis refers to the presence of redness on the surface of skin associated with small capillary vessels mainly localized on the face or sometimes the low neckline. Neoangiogenesis (neovascularization or synthesis of new blood vessels) is undoubtedly present in an outbreak of this redness, leading to telangiectasias (noticeable small vessels) [9]. The initial stimulus remains poorly understood, although the sun and other environmental factors have been suggested as causes of this phenomenon.

The effect of repeated vasomotor reactions is lesions of the lymphatic network responsible for persistent inflammation, which is embarrassing for the person.

This induces the activation of cells capable of producing proinflammatory molecules, angiogenic growth factors such as VEGF and FGF2 and proteases such as metalloproteinases (MMPs). MMPs degrade the extracellular matrix of skin tissue thus releasing angiogenic growth factors, and degrade the vascular wall enabling endothelial cells to migrate [10]. Neoangiogenesis is the formation of new vessels from existing vessels via morphological and functional changes of vascular endothelial cells. A high level of VEGF expression has been measured in the skin of people presenting with redness [11, 12].

Furthermore, cathelicidins may also trigger hypervascularity and angiogenesis in an outbreak of skin redness [5, 13].

The key steps of angiogenesis are as follows:
Release of deleterious mediators by surrounding cells: cytokines, proteases such as MMPs, and proangiogenic growth factors;
Equilibrium shifts in favor of the proangiogenic mediators VEGF/FGF2 (or bFGF), which are:
  Secreted by surrounding cells,
  Released from the extracellular matrix by MMPs;
Activation of endothelial cells
Degradation of the vascular wall by MMPs
Migration and proliferation of endothelial cells
Formation of new vessels In an outbreak of skin redness, sun exposure, oxidative stress and certain microbes are factors that trigger and exacerbate the unsightly phenomenon.

3—Role of Bacteria and Parasites

*Demodex folliculorum* is a saprophyte parasite (mite) colonizing the pilosebaceous follicle whose density may increase during skin redness. A bacterium, *Bacillus oleronius*, was isolated from Demodex: one parasite contained 40 bacteria. This *B. oleronius* bacterium induces the proliferation of mononuclear cells and causes an inflammatory response in patients presenting with redness associated with pustules. Moreover, *B. oleronius* releases molecules that stimulate innate immunity via TLRs.

4—Oxidative Stress and Sun

Reactive oxygen species (ROS) are increased in erythrocouperosis lesions but the exact location of these ROS has not been determined. The cells from which ROS arise are leucocytes and keratinocytes. Following the release of ROS, a cascade of cellular signals is established to induce the production of proinflammatory mediators (TNFα by keratinocytes) and MMPs (by fibroblasts). Thus, ROS contribute to the damaging of dermal and vascular material and to the inflammatory response.

UV rays cause flushes and aggravate skin redness. UV rays induce angiogenesis in mice and stimulate the production of VEGF and FGF2 in keratinocytes and in the skin of mice. UV rays also generate ROS and stimulate the production of inflammatory mediators (IL8) and MMPs. UV rays stimulate the TLR2 pathway and in particular induce the production of LL37. UV rays qualitatively and quantitatively alter the dermal connective tissue that promotes the vasculature. The mediators (inflammatory, angiogenic and MMPs) produced by UV rays destroy the vascular wall and stimulate endothelial cells, thus enabling extravasation, vasodilatation and inflammation. Thus, the anomalies of the elastic material (elastosis) and the collagenous material constitutes a poor support for the vessels and contributes to the formation of erythema and telangiectasias. UV rays thus induce dermal and vascular lesions [1].

PRIOR ART

Few compounds are known for the cosmetic prevention and/or treatment of skin redness. Hemp oil is known to attenuate the symptoms. In the case of bacterial attack, antibiotic creams may be prescribed. Topical steroids can have a short-term effect, but in the long term they have a tendency to aggravate the symptoms of couperosis. Laser treatments can destroy the superficial vessels of the patient's skin for a few years, although this costly treatment must be repeated regularly.

Compositions containing chitosan and a short/medium chain dicarboxylic acid amide, forming a film after application on the skin, have been described to prevent and treat skin redness (WO 2009/150257). Compositions containing modulators of pituitary adenylate cyclase-activating polypeptide (PACAP) receptors also have been proposed to decrease skin redness (WO 2010/007175). Plant-based compositions have also been described, such as:

Compositions comprising green tea and/or soy extracts, in combination with *ginkgo biloba* leaves extracts (FR2885301);
Compositions comprising caffeine (FR2855050);
Compositions comprising lupin peptides possessing metalloproteinase inhibition properties (WO 00/62789).

Arabinogalactans

Arabinogalactans (also called galactoarabinans) are polysaccharides. They are present in variable quantities in a number of plants, fungi and bacteria. Arabinogalactans are natural soluble fibers that can be extracted from bacteria or from plants such as coffee or larches.

Arabinogalactan is a polymer composed of two types of saccharides, galactose and arabinose, in a ratio of 6:1, respectively.

Methods for extracting arabinogalactan have been described, in particular from coffee (EP 1 600 461, WO 2007/099997) and from larch (EP 0 866 808). The most common commercially-available arabinogalactans are those from larch, a tree that is particularly arabinogalactan-rich.

Arabinogalactan has numerous effects on mammalian metabolism; for example, mention may be made of the following effects:

Arabinogalactans are indigestible fibers having a prebiotic action, i.e., one that promotes the proliferation, in the digestive tract, of bacteria useful for the body.
Arabinogalactan is known to stimulate the immune system. The application EP 1 600 461 claims in particular the addition of arabinogalactan in foods in order to obtain "health foods." Arabinogalactan stimulates the secretion of interleukin-12, which promotes DNA repair (FR2836378).
The application WO 2010/020379 describes compositions comprising arabinogalactan for the prevention and treatment of allergic and inflammatory diseases: arabinogalactan has the property of significantly decreasing the secretion of IgE.
The application WO 2010/052327 describes arabinogalactan as being an active compound for the prevention of stretch marks. Indeed, arabinogalactan has the following properties:
it promotes the renewal of cells, notably fibroblasts;
it stimulates the expression of collagens type I and III;
it inhibits the secretion of IL-1β.

In a completely surprising manner, the inventors of the present application have demonstrated another beneficial effect of arabinogalactan on the cosmetic treatment and prevention of skin redness. Arabinogalactan indeed has advantageous properties in terms of limiting the proliferation of endothelial cells during episodes of redness of the skin. Furthermore, its anti-redness action is stimulated when it is used in combination with lupin peptides.

DESCRIPTION OF THE INVENTION

The present invention relates to a cosmetic method for preventing and/or treating skin redness, comprising the administration of a composition comprising arabinogalactan to a person likely to form redness or having redness.

The composition may further include other anti-redness compounds such as, in particular, lupin peptides. Such a combination exhibits synergistic effects on the various molecular phenomena intervening in an outbreak of redness.

DETAILED DESCRIPTION OF THE INVENTION

By virtue of its properties of regulating innate immunity phenomena and neoangiogenesis, arabinogalactan makes it possible to decrease the reactivity of certain skin types likely to develop redness, and thus to prevent and treat an outbreak of this redness. The arabinogalactan being from a plant, one of the advantages of the invention is to provide people prone to skin redness, and thus having particularly sensitive skin, a composition comprising essentially natural substances.

The expression "skin redness" refers to facial erythemas and telangiectasias of any origin.

The expression "prevention of skin redness," according to the present invention, refers to an action making it possible to avoid or at the very least to reduce the formation of unsightly redness by application of the composition before and during an event known to be capable of causing an outbreak of redness, such as sun exposure or stress.

The expression "treatment of skin redness," according to the present invention, refers to an action making it possible to decrease unsightly symptoms by application of the composition on noticeable redness.

The expression "composition comprising arabinogalactan," according to the present invention, means that the "arabinogalactan" compound is the active ingredient of the composition, i.e., it has its own action, as-is, on the prevention and treatment of skin redness. As shown in the examples, arabinogalactan acts on various molecular factors involved in an outbreak of redness: inhibition of the expression of LL37, inhibition of the proliferation of endothelial cells, and inhibition of the expression of VEGF.

The expression "person likely to form or having redness" refers a person judging redness on the face as unsightly and disabling, regardless of the stage at which this redness may be classified from a clinical point of view.

According to a preferred aspect of the invention, said composition is administered topically, in particular on areas of skin likely to form redness, and notably the face.

The composition may also be administered orally, notably in the form of tablets, capsules, soft capsules, pills, emulsions, gels, or in the form of dietary supplements or food products.

According to a preferred aspect of the invention, the arabinogalactan used is extracted from larch. An extraction method is described in particular in the patent application EP 0 866 808. According a preferred aspect of the invention, the larch from which the arabinogalactan arises is cultivated in a cautious and sustainable manner. The arabinogalactan may also be extracted from grasses, notably meadow foxtail, timothy, orchard grass or rye.

Preferentially, the anti-redness composition of the invention comprises arabinogalactan in a proportion of between 0.01% and 10% by weight, advantageously between 1% and 5%, and more preferentially in a proportion of about 2% by weight in relation to the total weight of the composition.

According to a preferred aspect of the invention, the anti-redness composition includes at least one other anti-redness agent selected in particular from the following list: lupin peptides, permethol, genistein, esculoside, dextran sulfate, hesperidin methyl chalcone, retinoids, licochalcone, oxymetazoline, kinetin, licorice extract, vitamin P-like, butcher's broom extract, *Sophora japonica, Hamamelis* extract, *Ruscus*, antibiotics such as doxycycline, polyphenols including tannins, phenolic acids, anthocyans, procyanidols, flavonoids with, for example, quercetin, extracts of green tea, red berries, cocoa, grape, *Passiflora incarnata, Citrus.*

Each one of these compounds has its own action aiming to amplify or promote the action of arabinogalactan on skin redness.

According to a preferred aspect of the invention, said composition comprises arabinogalactan and lupin peptides.

The expression "lupin peptides" refers to any preparation comprising a peptide-enriched lupin extract, such as, for example, the following preparations:

the lupin protein hydrolysates Structurine® and Anageline®, sold by Silab;

the lupin peptide hydrolysate Sweet Blue Lupine Peptides®, sold by Oat Cosmetics.

A preferred preparation of lupin peptides is the preparation sold by Laboratoires Expanscience, obtained by the method described in the application WO2005/102259.

In particular, the composition of the invention comprises between 0.01% and 10% of arabinogalactan, and between 0.01% and 10% of lupin peptides.

A preferred composition comprises 2% of arabinogalactan and 0.2% of lupin peptides.

According to a preferred aspect of the invention, the anti-redness composition further comprises at least one soothing and repairing agent, selected in particular from the following agents:

a quinoa peptide extract
an oxazoline
a sunflower oil concentrate
a vitamin E acetate
as well as the various mixtures of these compounds.

Each one of these compounds has its own action aiming to amplify, supplement or promote the action of arabinogalactan and, optionally, lupin peptides on skin prone to redness.

The expression "quinoa peptide extract" refers notably to an extract of quinoa seeds as described in the international application WO2008/080974, this extract being characterized in that it comprises 10% to 90% by weight of peptides and 10% to 50% by weight of sugars in relation to the total weight of said extract, and being used for its barrier repair and anti-inflammatory properties.

The sunflower oil concentrates that may be used in the context of the present invention in combination with arabinogalactan are advantageously linoleic sunflower concentrates, such as the active agent sold by Laboratoires Expanscience, Saline® (see international application WO 01/21150) notably for their repairing and anti-irritation and/or soothing activity.

The oxazolines that may be used in the context of the present invention in combination with arabinogalactan are advantageously oxazolines selected from the group comprised of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline and 2-undecyl-4-ethyl-4-hydroxymethyl-1,3-oxazoline. More advantageously, said oxazoline is 2-undecyl-4,4-dimethyl-1, 3-oxazoline, called OX-100 or Cycloceramide® (see international applications WO2004050052, WO2004050079 and WO2004112741). They are particularly useful for their anti-inflammatory and/or anti-irritation and/or soothing activity.

The composition of the invention may further include at least one compound selected from the group comprised of moisturizing and/or healing and/or repairing and/or anti-irritant and/or soothing and/or antioxidant and/or anti-aging agents.

The moisturizing/emollient active agents may be glycerin or derivatives thereof, urea, pyrrolidone carboxylic acid and derivatives thereof, hyaluronic acid of any molecular weight, glycosaminoglycans and any other polysaccharides of marine, plant or biotechnological origin such as, for example, xanthan gum, Fucogel®, certain fatty acids such as lauric acid, myristic acid, polyunsaturated and monounsaturated omega-3, -6, -7 and -9 fatty acids such as linoleic acid and palmitoleic acid, and certain types of butter such as Shea butter.

The healing and/or cutaneous barrier repairing agents that may be used in combination are advantageously panthenol (vitamin B5), zinc oxide, madecassic or asiatic acid, dextran sulfate, coenzyme Q10, glucosamine and derivatives thereof, chondroitin sulfates and on the whole glycosaminoglycans, dextran sulfate, ceramides, cholesterol, squalane, phospholipids. PPAR (rosiglitazone, pioglitazone), RXR and LXR agonists may also be used.

The anti-inflammatory and/or anti-irritant and/or soothing agents may be glycyrrhetinic acid (licorice derivatives) and salts and esters thereof, lipoic acid, beta-carotene, vitamin B3 (niacinamide, nicotinamide), vitamin E, vitamin C, vitamin B12, lycopene or lutein, spring water or thermal spring water (eau d'Avène, eau de la Roche Posay, eau de Saint Gervais, eau d'Uriage, eau de Gamarde), or topical disulone, or steroidal anti-inflammatory drugs (SAIDs), such as corticoids, or non-steroidal anti-inflammatory drugs (NSAIDs). Mention may also be made of isoflavones, notably soy isoflavones such as, for example, genistein/genistin, daidzein/daidzin.

The antioxidants that may be used in combination are advantageously selected from the group composed of thiols and phenols, licorice derivatives such as glycyrrhetinic acid and salts and esters thereof, alpha-bisabolol, lipoic acid, vitamin B12, vitamin B3 (niacinamide, nicotinamide), vitamin C, vitamin E, coenzyme Q10, krill, glutathione, butylated hydroxytoluene (BHT), butylated hydroxyanisole (BHA), lycopene or lutein, beta-carotene. The group of antioxidants further includes anti-glycation agents such as carnosine or certain peptides, N-acetyl-cysteine, as well as antioxidant or free-radical scavenging enzymes such as superoxide dismutase (SOD), catalase, glutathione peroxidase, thioredoxin reductase and agonists thereof.

The anti-aging agents may be vitamin C, hyaluronic acid of any molecular weight, retinoids such as retinol, retinal and retinoids; in particular nonaromatic retinoids such as retinaldehyde, tretinoin, isotretinoin and 9-cis retinoic acid, vitamin A, monoaromatic retinoids such as etretinate, all-trans acitretin and motrerinide, and polyaromatic retinoids such as adapalene, tazarotene, tamibarotene and sulfone methyl arotinoid.

Moreover, the composition of the invention may also include inorganic or organic filters and sunscreens (pigmentary or ultrafine), antifungal compounds, preservatives and antibacterial agents.

The sun protection active agents that may be used in combination are advantageously UVB and/or UVA filters or sunscreens, such as the inorganic and/or organic screens or filters known to persons skilled in the art, who will adapt their choice and their concentrations according to the degree of protection sought. As examples of sun protection active agents, particular mention may be made of titanium dioxide, zinc oxide, methylene bis-benzotriazolyl tetramethylbutylphenol (brand name: Tinosorb M) and bis-ethylhexyloxyphenol methoxyphenyl triazine (brand name: Tinosorb S), octocrylene, butyl methoxydibenzoylmethane, terephthalylidene dicamphor sulfonic acid, 4-methylbenzylidene camphor, benzophenone, ethylhexyl methoxycinnamate, ethylhexyl dimethyl PABA and diethylhexyl butamido triazone.

The antifungal compounds that may be used in combination are advantageously econazole and ketoconazole.

The preservatives that may be used in combination are, for example, those generally used in cosmetics or nutraceuticals, molecules with anti-bacterial activity (pseudo-preservatives) such as caprylic derivatives like, for example, caproyloyl glycine and glyceryl caprylate, such as hexanediol and sodium levulinate, zinc and copper derivatives (gluconate and PCA), phytosphingosine and derivatives thereof, benzoyl peroxide, piroctone olamine, zinc pyrithione and selenium sulfide. The antiseptic preservatives that may be used in combination are, for example, triclosan, chlorhexidine and quaternary ammonium.

The antibiotics that may be used in combination are advantageously fusidic acid, penicillin, tetracyclines, pristinamycin, erythromycin, clindamycin, mupirocin, minocycline and doxycycline. The antiviral agents that may be used in combination are advantageously acyclovir and valacyclovir.

Among the active agents recommended in combination with the extract of the invention, mention may be made of plant extracts, in particular:

Plant oils such as soy oils and/or rapeseed oil, avocado oil (WO2004/012496, WO2004/012752, WO2004/016106, WO2007/057439), lupin oil, advantageously sweet white lupin oil (WO 98/47479), squash seed oil (sebum-regulating), Melaleuca oil (antidandruff), borage oil (antidandruff), cade oil;

oleodistillates or concentrates of plant or animal oil, in particular of sunflower oil, more advantageously linoleic sunflower concentrates, such as the active agent sold by Laboratoires Expanscience, Saline® (see international application WO 01/21150), of avocado, rapeseed, corn or palm oil, useful notably for their moisturizing and/or emollient, healing and/or cutaneous barrier repairing, anti-inflammatory and/or anti-irritation and/or soothing activity;

plant or plant oil unsaponifiables, advantageously Avocadofurane® (avocado furans, which may be obtained by the method described in the international application WO 01/21605), avocado and soy unsaponifiables, more particularly a mixture of avocado furanic unsaponifiables and soy unsaponifiables, in a respective ratio of about 1:3-2:3 (such as Piascledine®), soy unsaponifiables (as obtained by the method described in the international application WO01/51596), sterol unsaponifiables (unsaponifiables whose sterols, methylsterols and triterpene alcohols content is between 20% and 95% by weight, preferably 45% to 65% by weight, in relation to the total weight of the unsaponifiable), phytosterols, esters of sterols and vitamin derivatives, useful notably for their healing and/or cutaneous barrier repairing, anti-aging, anti-inflammatory activity;

peptides or complexes of plant amino acids, in particular avocado peptides (such as those described in the international application WO2005/105123), lupin peptides (such as those obtained by the method described in the application WO2005/102259), quinoa peptides (such as those described in the international application WO2008/080974), maca peptides (such as those described in the international application WO2004/112742), fermented or unfermented soy peptides, rice peptides (such as those described in the international application WO 2008/009709), useful notably for their moisturizing and/or emollient (avocado), keratoregulating (lupin, quinoa), healing and/or cutaneous barrier repairing (maca, quinoa, soy), anti-inflammatory and/or anti-irritation and/or soothing (lupin, quinoa, *Schisandra*), antioxidant (avocado), anti-aging (lupin, maca, avocado) and pigmenting (rice) activity;

plant sugars, in particular avocado sugars (such as those described in the application WO2005/115421), useful notably for their keratoregulating, healing and/or barrier cutaneous repairing, anti-inflammatory and/or anti-irritation and/or soothing action;

5-α Avocuta® (butyl avocadate), a 5-α reductase inhibitor (see WO 01/52837 and WO 02/06205) and regulator of the increased seborrhea secretions found in acne or dandruff;

polyphenol-enriched avocado fruit extract (as described in the application FR 1 061 055);

maca leaves extract (as described in the application FR 1 061 047);

*Gynandropsis gynandra* extract (as described in the application FR 1 061 051);

lupeol (FR 2 822 821, FR 2 857 596) useful notably to support wound healing, total lupin extract (such as those described in the international application WO2005/102259), particularly suited for the treatment of irritation;

isoflavones such as, for example, soy isoflavones;

cupuaçu butter, particularly appreciated for its moisturizing properties;

peptide and sugar extract of *Acacia macrostachya* seeds (FR 0958525), suited for its moisturizing properties;

*Vigna unguiculata* seed extract (FR 0958529);

*Schisandra sphenanthera* fruit extract (such as those described in the applications FR 0955344 and WO 2011/012612) and *Schisandra* peptide extract (FR 0955343 and WO 2011/012615) suited for its anti-inflammatory and anti-acne properties.

The topical composition of the invention also comprises a suitable carrier, which may be any carrier among those known to persons skilled in the art in order to obtain a cosmetic composition that may be used according to the invention, in particular in the form of a cream, lotion, gel, spray, patch, water, pomade, milk or oil, optionally in the form of an emulsion, with in addition components known to persons skilled in the art to improve, modify or stabilize the composition from a cosmetics point of view.

For oral ingestion, numerous forms of realization, and notably dietary supplements, are possible. They are formulated by the usual methods to produce tablets, capsules, soft capsules, pills, emulsions and gels. In particular, the arabinogalactan and the other active agents of the invention may be incorporated in all forms of dietary supplements or enriched foods, for example, food bars, compressed or uncompressed powders, beverages, dairy products and in particular yogurts and drinkable yogurts. The powders may be diluted in water, sodas, fruit juices, dairy products or soy- or rice-based products, or may be incorporated in food bars.

The operating conditions for preparing these compositions of the invention are part of the general knowledge of persons skilled in the art.

The present invention also relates to a cosmetic use of arabinogalactan to prevent and/or treat an outbreak of redness on the skin.

The present invention also relates to a cosmetic use of a combination of arabinogalactan and lupin peptides to prevent and/or treat an outbreak of redness on the skin.

The present invention also relates to a therapeutic composition comprising arabinogalactan for its use in the prevention and/or treatment of skin redness.

The invention also relates to a method for preventing and/or treating skin redness, comprising the topical or oral administration of a composition comprising arabinogalactan.

The present invention also relates to a composition comprising arabinogalactan and lupin peptides for its use in the prevention and/or treatment of skin redness.

The invention also relates to a method for preventing and/or treating skin redness, comprising the topical or oral administration of a composition comprising arabinogalactan and lupin peptides.

The present invention also relates to a composition comprising arabinogalactan for its use in the prevention and/or treatment of rosacea.

Indeed, redness may be associated with the early stages of rosacea, a benign chronic skin disorder, primarily affecting the face and resulting in flushes, permanent erythema, papules, pustules and telangiectasias. Four stages of rosacea have been proposed:

Stage I: erythematotelangectasic rosacea: flushes, persistent erythema and telangiectasias;

Stage II: rosacea or papulopustular rosacea: persistent erythema, papules and pustules;

Stage III: phymas or phymatous rosacea;

Stage IV: ocular rosacea.

The invention also relates to a method for preventing and/or treating rosacea, comprising the topical or oral administration of a composition comprising arabinogalactan.

The present invention also relates to a composition comprising arabinogalactan and lupin peptides for its use in the prevention and/or treatment of rosacea.

The invention also relates to a method for preventing and/or treating rosacea, comprising the topical or oral administration of a composition comprising arabinogalactan and lupin peptides.

EXAMPLES

In the in vitro examples, the active agents are diluted at a concentration of 0.2% for arabinogalactan, and 0.02% for lupin peptides; in the final cosmetic compositions, the concentrations used will be ten times higher (2% of arabinogalactan, 0.2% of lupin).

1. The Effects of Arabinogalactan and the Combination of Arabinogalactan and Lupin Peptides on the Gene Expression of Kallikrein-5 (KLK5) and Cathelicidin (LL37)

In order to evaluate the potential activity of arabinogalactan, optionally in combination with lupin peptides, in the inflammatory phase of skin redness, we studied the effect of this complex of active agents on the gene expression of cathelicidin (LL37) and kallikrein-5 (KLK5) induced by a vitamin D analogue (calcitriol) in keratinocytes.

Materials and Methods

Normal human epidermal keratinocytes (NHEK) were cultured in differentiation culture medium supplemented with $Ca^{++}$.

The keratinocytes were treated for 24 hours with the arabinogalactan (ARG)/lupin peptides (LUP) active agents at concentrations of 0.2%/0.02% alone or in combination; in the presence or absence of calcitriol (vitamin D analogue).

At the end of the treatment, the culture supernatants were removed and total RNA was extracted, analyzed and assayed. The neo-synthesized cDNA relating to the genes of interest (LL37 and KLK5) or to the reference genes were amplified selectively by iQ5 real-time PCR (Biorad) using SybrGreen technology.

For each sample, the expression level of the gene of interest was normalized by the expression level of most stable reference gene (the GAPDH gene). By calculating ΔCt ($Ct_{gene\ of\ interest} - Ct_{reference\ gene}$) and ΔΔCt ($\Delta Ct_{control} - \Delta Ct_{treated}$) the relative quantity of the gene of interest was measured: $RQ = (1+E)^{\Delta\Delta Ct}$; when E (effectiveness) is equal to 1, then $RQ = 2^{\Delta\Delta Ct}$.

The significance of the results was verified for the ΔCt values by a single-factor analysis of variance followed by a Tukey's test.

The percentage of inhibition of the expression of LL37 and KLK5 is thus calculated:

[(RQ(stim calcitriol)−RQ(active treatment))/RQ(stim calcitriol)]*100

Results

Figure 2:
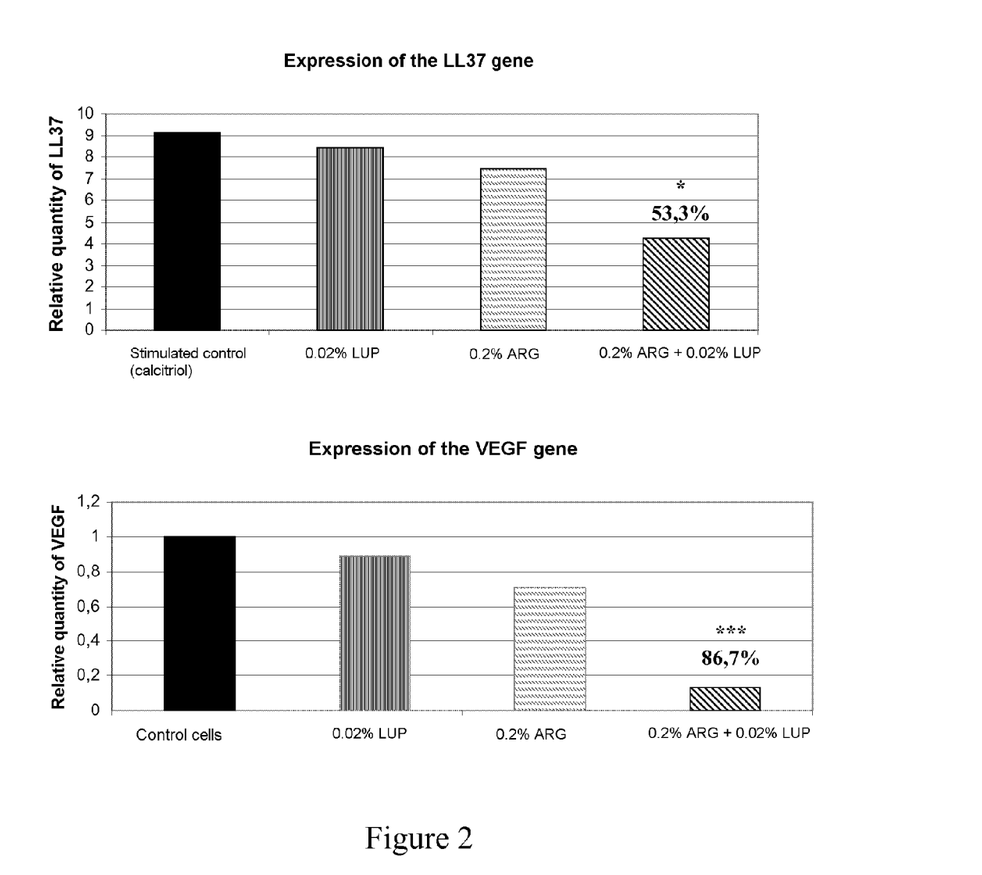
FIG. 2: Synergy of the effects of the combination of arabinogalactan and lupin peptides on the expression of LL37 and VEGF.

Gene Expression of LL37 (Table 1 and FIG. 2):

Calcitriol strongly and significantly stimulated the gene expression of LL37 by keratinocytes (+812%, p<0.001).

Arabinogalactan used at a concentration of 0.2% significantly inhibits by 18% the expression of LL37. The combination of arabinogalactan+lupin peptides active agents inhibits by 53% the gene expression of LL37 induced by calcitriol. This inhibition results from the synergistic effect of the combination of arabinogalactan with lupin peptides. Indeed, tested alone, these active agents inhibit the expression of LL37 more moderately.

TABLE 1

| | Mean ΔCt ($Ct_{LL37} - Ct_{GAPDH}$) | Standard deviation | ΔΔCt | LL37 expression (relative quantity) | Percentage of inhibition |
|---|---|---|---|---|---|
| Control cells | 14.21 | 0.69 | | 1.00 | |
| Stimulated control (calcitriol) | 11.02 | 0.28 | 3.19 | 9.12 $$$ | |
| 0.2% ARG | 11.31 | 0.57 | 2.9 | 7.46 * | 18.2% |
| 0.02% LUP | 11.14 | 0.66 | 3.07 | 8.39 ns | 7.9% |
| 0.2% ARG + 0.02% LUP | 12.12 | 1.10 | 2.09 | 4.25 ** | 53.3% |

$$$: p < 0.001 versus control cells
**: p < 0.01;
*: p < 0.05 versus stimulated control;
ns: not significant Gene Expression of KLK5 (Table 2):

Calcitriol strongly and significantly stimulated the gene expression of kallikrein-5 by keratinocytes (+149%, p<0.001).

The combination of arabinogalactan+lupin peptides active agents clearly inhibited the gene expression of KLK5 induced by calcitriol (39% inhibition).

TABLE 2

| | Mean ΔCt ($Ct_{KLK5} - Ct_{GAPDH}$) | Standard deviation | ΔΔCt | KLK5 expression (relative quantity) | Percentage of inhibition |
|---|---|---|---|---|---|
| Control cells | 3.78 | 0.99 | 0 | 1.00 | |
| Stimulated control (calcitriol) | 2.46 | 1.35 | 1.32 | 2.49 $$$ | |
| 0.2% ARG + 0.02% LUP | 3.18 | 1.25 | 0.6 | 1.52 | 39.3% |

$$$: p < 0.001 versus control cells

Conclusion

Under these experimental conditions, the combination of arabinogalactan+lupin peptides active agents made it possible to modulate in a synergistic manner the expression of cathelicidin (LL37), as well as of the enzyme responsible for its maturation, kallikrein-5.

Thus, the combination of arabinogalactan and lupin peptides contributes to modulate the induction of the immune and inflammatory response dependent on the TLR2/KLK5/LL37 pathway in an outbreak of skin redness.

2. Activity on Vascular Parameters: Proliferation of Endothelial Cells

Materials and Methods

Normal human dermal microvascular endothelial cells were incubated for 24 or 48 hours in the absence (control) or in the presence of the arabinogalactan (ARG)/lupin peptides (LUP) active agents at concentrations of 0.2%/0.02% alone or in combination and in the presence of vascular endothelial growth factor (VEGF), the reference activator. At the end of incubation, the viability of the cells was evaluated by a spectrophotometric method: P-nitrophenyl phosphate (PNPP) is transformed into p-nitrophenol by phosphatases of viable cells and the absorbance at 405 nm of p-nitrophenol is directly proportional to the number of viable cells.

The results are expressed as the percentage of the "PNPP" signal of the control without VEGF at T0 (mean±standard deviation).

The statistical significance of the differences between the "VEGF stimulated cells" and "VEGF+active agents" conditions was evaluated by a single-factor analysis of variance followed by a Holm-Sidak test.

The percentage of inhibition of proliferation is calculated according to the following equation:

[(active treatment)−(VEGF stimulated)/(control without VEGF)−(VEGF stim)]*100

Results 2.1. Proliferation of Endothelial Cells in the Presence of VEGF (Table 3):

VEGF, an angiogenic factor, stimulates the growth of endothelial cells in relation to control cells (not treated with VEGF): +78.9% (p<0.01) after 24 hours of incubation and +159% (p<0.01) after 48 hours of incubation.

In the presence of arabinogalactan, this stimulation of growth decreases from 17% at 24 hours to nearly 10% at 48 hours.

In the presence of the combination of arabinogalactan+lupin peptides, the proliferation of endothelial cells induced by VEGF is significantly inhibited (50% and 25% inhibition at 24 and 48 hours, respectively), with a synergistic action of the two active agents.

TABLE 3

| | T24 h - %/control (without VEGF) T0 | Percentage of inhibition 24 h | T48 h - %/control (without VEGF) T0 | Percentage of inhibition 48 h |
|---|---|---|---|---|
| Control cells without VEGF | 163.3 ± 8 | | 162.8 ± 8.3 | |
| VEGF stimulated controls | 213.2 ± 10.8 | | 262.6 ± 5 | |
| 0.2% ARG | 204.7 ± 7.1 | 17.03% | 252.9 ± 6 | 9.71% |
| 0.02% LUP | 209.1 ± 6.4 | 8.22% | 259.3 ± 7.2 | 3.31% |
| 0.2% ARG + 0.02% LUP | 187.3 ± 4.1 | 50.90% p < 0.05 | 237.2 ± 9.9 | 25.45% p < 0.05 |

Arabinogalactan, by limiting the proliferation of endothelial cells, contributes to limit the early phase of angiogenesis.

The combination of arabinogalactan+lupin peptides is more effective than arabinogalactan alone in limiting this cell proliferation.

2.2. Gene Expression Markers of Angiogenesis: VEGF, FGF2, HIF1α, Thrombospondin

In order to understand the antiangiogenic effect of arabinogalactan, the gene expression by keratinocytes of certain markers involved in angiogenesis was studied.

Expression of VEGF and FGF2, proangiogenic growth factors:

Vascular endothelial growth factor (VEGF) is the principal growth factor of the vascular endothelium. It is a powerful vasoactive and inflammatory cytokine that acts directly on endothelial cells by stimulating their migration and their proliferation, and thus promotes neoangiogenesis. Moreover, VEGF leads to an increase in the permeability of endothelial cells, whose plasma proteins then flow into the extracellular matrix (vascular hyperpermeability). VEGF has chemotactic properties that enable the recruitment of inflammatory cells. VEGF is secreted by keratinocytes, fibroblasts, mast cells, inflammatory cells and endothelial cells. VEGF and its receptors are increased in the lesions of subjects presenting with skin redness [12].

FGF2 or bFGF: a growth factor synthesized by keratinocytes, fibroblasts, inflammatory cells and endothelial cells and a powerful regulator of angiogenesis in synergy with VEGF.

HIF1α, a VEGF transcription factor,

Thrombospondin, an antiangiogenic factor.

Materials and Methods

Normal human epidermal keratinocytes (NHEK) were incubated in the presence of the complex of arabinogalactan (ARG)/lupin peptides (LUP) active agents at concentrations of 0.2%/0.02% alone or in combination.

At the end of the treatment, the culture supernatants were removed and total RNA was extracted, analyzed and assayed. The neo-synthesized cDNA relating to the genes of interest (VEGF, FGF2, HIF1α, THBS1) or to the reference genes were amplified selectively by iQ5 real-time PCR (Biorad) using SybrGreen technology.

For each sample, the expression level of the gene of interest was normalized by the expression level of most stable reference gene (the GAPDH gene). By calculating $\Delta Ct$ ($Ct_{gene\ of\ interest} - Ct_{reference\ gene}$) and $\Delta\Delta Ct$ ($\Delta Ct_{control} - \Delta Ct_{treated}$) the relative quantity of the gene of interest was measured: $RQ = (1+E)^{\Delta\Delta Ct}$; when E (effectiveness) is equal to 1, then $RQ = 2^{\Delta\Delta Ct}$.

The significance of the results was verified for the $\Delta Ct$ values by a single-factor analysis of variance followed by a Dunnett's test.

The percentage of inhibition is calculated for VEGF, FGF2 and HIF1α:

[(RQ(control)−RQ(active treatment))/RQ (control)]*100

The percentage of stimulation is calculated for THBS1:

[(RQ(active treatment)−RQ(control))/RQ (control)]*100

Results 2.2.1. Gene Expression of VEGF (Table 4 and FIG. 2):

Arabinogalactan significantly inhibits the expression of VEGF by 29%.

The combination of the arabinogalactan/lupin peptides active agents very strongly and significantly inhibited the expression of VEGF by keratinocytes (86% inhibition) and in a much more superior manner than the active agents tested alone. This inhibition results from the synergistic effect of the combination of arabinogalactan with lupin peptides.

TABLE 4

|  | Mean $\Delta Ct$ ($Ct_{VEGF} - Ct_{GAPDH}$) | Standard deviation | $\Delta\Delta Ct$ | VEGF expression (relative quantity) | Percentage of inhibition |
|---|---|---|---|---|---|
| Control cells | 8.53 | 0.58 |  | 1 |  |
| 0.2% ARG | 9.03 | 0.62 | −0.5 | 0.707 ** | 29.3% |
| 0.02% LUP | 8.7 | 0.98 | −0.17 | 0.889 ns | 11.1% |
| 0.2% ARG + 0.02% LUP | 11.44 | 1.34 | −2.91 | 0.133 *** | 86.7% |

***: $p < 0.001$;
**: $p < 0.01$ versus control cells;
ns: not significant 2.2.2. Gene Expression of FGF2 (Table 5):

The combination of arabinogalactan/lupin peptides active agents completely and significantly inhibited the expression of FGF2 by keratinocytes.

TABLE 5

|  | Mean $\Delta Ct$ ($Ct_{FGF2} - Ct_{GAPDH}$) | Standard deviation | $\Delta\Delta Ct$ | FGF2 expression (relative quantity) | Percentage of inhibition |
|---|---|---|---|---|---|
| Control cells | 6.97 | 0.83 |  | 1 | 1 |
| 0.2% ARG + 0.02% LUP | 14.34 | 1.37 | −7.37 | 0.006 *** | 99.4% |

***: $p < 0.001$ versus control cells 2.2.3. Gene Expression of HIF1α (Table 6):

The combination of arabinogalactan/lupin peptides active agents significantly inhibited the expression of the transcription factor HIF1α by keratinocytes (54% inhibition).

TABLE 6

|  | Mean $\Delta Ct$ ($Ct_{HIF1\alpha} - Ct_{GAPDH}$) | Standard deviation | $\Delta\Delta Ct$ | HIF1α expression (relative quantity) | Percentage of inhibition |
|---|---|---|---|---|---|
| Control cells | 5.5 | 1.3 |  | 1 |  |
| 0.2% ARG + 0.02% LUP | 6.63 | 1.22 | −1.13 | 0.456 ** | 54.3% |

**: $p < 0.01$ versus control cells 2.2.4. Gene Expression of Thrombospondin-1 (Table 7):

The combination of arabinogalactan/lupin peptides active agents significantly stimulated the expression of thrombospondin, an antiangiogenic factor, by keratinocytes (76% increase).

TABLE 7

|  | Mean $\Delta Ct$ ($Ct_{THBS1} - Ct_{GAPDH}$) | Standard deviation | $\Delta\Delta Ct$ | THBS1 expression (relative quantity) | Percentage of stimulation |
|---|---|---|---|---|---|
| Control cells | 4.34 | 1.8 | 0 | 1 |  |
| 0.2% ARG + 0.02% LUP | 3.52 | 1.44 | 0.82 | 1.765 * | 76.5% |

*: $p < 0.05$ versus control cells

Conclusion

Under the experimental conditions presented above, we have demonstrated that the combination of arabinogalactan/ lupin peptides active agents modulates the expression of factors involved in the induction of angiogenesis, in favor of an antiangiogenic effect. Indeed, the active agents may decrease the expression of proangiogenic markers (FGF2, VEGF) and increase the expression of an antiangiogenic marker (THBS1). Moreover, an inhibitory effect was also observed on the transcription factor of VEGF (HIF1α), suggesting regulation by the active agents upstream of VEGF via its transcription factor.

Thus at the expense of angiogenesis, an early phenomenon of neovascularization, the combination of arabinogalactan and lupin peptides contributes to limit the activation of endothelial cells and the synthesis of new blood vessels.

2.3. Gene Expression of MMP2 and MMP9, Markers of Neovascularization

The effect of the combination of arabinogalactan/lupin peptides active agents was sought on genes involved in the molecular phenomena of neovascularization.

Thus, the gene expression of two matrix metalloproteinases was studied, namely MMP2 and MMP9, responsible for degrading the extracellular matrix and which promote the migration of endothelial cells, a stage of angiogenesis, required for the formation of new blood vessels.

The effect of the active agents was sought in a basal condition (to study MMP2) or in a preventive manner on a cell layer having been subjected to inflammatory stress induced by PMA (for MMP9).

Materials and Methods

Normal human epidermal keratinocytes (NHEK) were pre-incubated for 24 hours in the presence of the arabinogalactan (ARG)/lupin peptides (LUP) active agents at concentrations of 0.2%/0.02%. PMA was then added for a total treatment period of 40 hours.

For the evaluation under basal conditions, the cells were simply incubated for 40 hours in the presence of the arabinogalactan (ARG)/lupin peptides (LUP) active agents at concentrations of 0.2%/0.02%.

At the end of the treatment, the culture supernatants were removed and total RNA was extracted, analyzed and assayed. The neo-synthesized cDNA relating to the genes of interest (MMP2, MMP9) or to the reference genes were amplified selectively by iQ5 real-time PCR (Biorad) using SybrGreen technology.

For each sample, the expression level of the gene of interest was normalized by the expression level of the most stable reference gene (the GAPDH gene). By calculating $\Delta Ct$ ($Ct_{gene\ of\ interest} - Ct_{reference\ gene}$) and $\Delta\Delta Ct$ ($\Delta Ct_{control} - \Delta Ct_{treated}$) the relative quantity of the gene of interest was measured: $RQ=(1+E)^{\Delta\Delta Ct}$; when E (effectiveness) is equal to 1, then $RQ=2^{\Delta\Delta Ct}$.

The significance of the results was verified for the $\Delta Ct$ values by a single-factor analysis of variance followed by a Dunnett's test (for MMP2) or a Tukey's test (for MMP9).

The percentage of inhibition is thus calculated for MMP2:

[(RQ(control)−RQ(active treatment))/RQ(control)]
*100

The percentage of inhibition is thus calculated for MMP9:

[(RQ(PMA stimulated)−RQ(active treatment))/RQ
(PMA stimulated)]*100

Results 2.3.1. Gene Expression of MMP2 (Table 8):

The combination of arabinogalactan/lupin peptides active agents significantly inhibited the gene expression of MMP2 (23% inhibition).

TABLE 8

| | Mean $\Delta Ct$ ($Ct_{MMP2} - Ct_{GAPDH}$) | Standard deviation | $\Delta\Delta Ct$ | MMP2 expression (relative quantity) | Percentage of inhibition |
|---|---|---|---|---|---|
| Control cells | 6.99 | 0.72 | | 1 | |
| 0.2% ARG + 0.02% LUP | 7.38 | 0.98 | −0.39 | 0.76 * | 23.7% |

*: $p < 0.05$ versus control cells 2.3.2. Gene Expression of MMP9 (Table 9):

PMA significantly and very strongly stimulated the gene expression of MMP9 in keratinocytes. Under these conditions, the combination of arabinogalactan and lupin peptides active agents made it possible to inhibit the gene expression of MMP9 induced by PMA (54% inhibition).

TABLE 9

| | Mean $\Delta Ct$ ($Ct_{MMP9} - Ct_{GAPDH}$) | Standard deviation | $\Delta\Delta Ct$ | MMP9 expression (relative quantity) | Percentage of inhibition |
|---|---|---|---|---|---|
| Control cells | 8.87 | 1.16 | | 1 | |
| Stimulated control (PMA) | 2.32 | 1.03 | 6.55 | 93.70 $$$ | |
| 0.2% ARG + 0.02% LUP | 3.46 | 0.7 | 5.41 | 42.51 * | 54.6% |

$$$: $p < 0.001$ versus control cells
*: $p < 0.05$ versus stimulated control

Conclusion

Under the experimental conditions described above, an inhibitory effect on the expression of matrix proteinases MMP2 and MMP9 was shown for the arabinogalactan/lupin peptides combination.

Thus, by reducing the degradation of the extracellular matrix, the active agents help limit the influx of endothelial cells, an early stage of neovascularization.

3. Activity on an Inflammatory Parameter: IL8

Materials and Methods

Human keratinocytes (NCTC 2544 cell line) were preincubated for 24 hours with the arabinogalactan (ARG)/lupin peptides (LUP) active agents at concentrations of 0.2%/0.02% or with the reference molecule, dexamethasone.

Inflammation was then induced by treatment with PMA for 24 hours, always in the presence of the active agents or the reference molecule.

At the end of incubation, the quantities of interleukin-8 (IL8) present in the culture supernatants were measured by ELISA.

The significance of the results was verified by a single-factor analysis of variance followed by a Tukey's test.

The percentage of inhibition is calculated according to the following formula:

[(stimulated PMA)−(active treatment)/(stimulated PMA)]*100

Results (Table 10)

The treatment by PMA clearly stimulated the release of IL8 by keratinocytes, whereas dexamethasone clearly inhibited this release (−81%); these results validate the test.

The combination of arabinogalactan+lupin peptides active agents significantly inhibited the release of IL8 induced by PMA (33% inhibition).

TABLE 10

| IL8 (ng/ml) | |
| --- | --- |
| Control cells | 0.1033 ± 0.002 |
| Stimulated control (PMA) | 30.60 ± 1.888 $$$ |
| $10^{-7}$ M Dexamethasone | 5.967 ± 0.203 80.5% *** |
| 0.2% ARG + 0.02% LUP | 20.40 ± 1.559 33.3% ** |

$$$: $p < 0.001$ versus control cells
***: $p < 0.001$;
**: $p < 0.01$ versus stimulated control Conclusion Under these experimental conditions, the combination of arabinogalactan+lupin peptides active agents has a modulating effect on the inflammatory mediator IL8.

General Conclusion

Arabinogalactan has the following effects:

an inhibiting action on the expression of LL37 (Table 1) and on the expression of VEGF (Table 4), a limitation of the proliferation of endothelial cells following stimulation by VEGF (Table 3).

This makes it a good active ingredient for the prevention and/or treatment of redness.

The combination of this active agent with lupin peptides makes it possible to obtain much better results, by an action on the majority of the factors involved in skin redness such as immune and inflammatory factors and vascular and dermal factors.

4. Examples of Compositions for Topical Application

The inventors present below several compositions for topical application. Arabinogalactan and lupin peptides may be incorporated in diverse cosmetic products such as cleansing waters, emulsions, creams, milks, lotions, foaming products and sprays, whose compositions are presented below.

SPF 20 Anti-Redness Emulsion

| | |
| --- | --- |
| AQUA (WATER) | q.s. to 100% |
| GLYCERIN | 1-15% |
| DICAPRYLYL CARBONATE | 1-10% |
| DICAPRYLYL ETHER | 1-10% |
| CAPRYLIC/CAPRIC TRIGLYCERIDE | 1-10% |
| GLYCERYL STEARATE | 1-5% |
| CHEMICAL SOLAR FILTERS | 1-10% |
| BUTYROSPERMUM PARKII (SHEA) BUTTER | 1-5% |
| CETYL ALCOHOL | 1-5% |
| DEXTRIN PALMITATE | 0-2% |
| LAURETH-23 | 0-2% |
| HYDROXYETHYL ACRYLATE/SODIUM ACRYLOYLDIMETHYL TAURATE COPOLYMER | 0-2% |
| PEG-75 STEARATE | 0-2% |
| CERA ALBA (BEESWAX) | 0-2% |
| PRESERVATIVES | 0-2% |
| CETETH-20 | 0-0.5% |
| STEARETH-20 | 0-0.5% |
| DECYL GLUCOSIDE | 0-0.5% |
| XANTHAN GUM | 0-0.5% |
| TOCOPHERYL ACETATE | 0-0.5% |
| CETEARYL ALCOHOL | 0-0.5% |
| CETYL PALMITATE | 0-0.5% |
| COCOGLYCERIDES | 0-0.5% |
| QUINOA PEPTIDE EXTRACT | 0.01-10% |
| CYCLOCERAMIDES | 0.01-10% |
| ARABINOGALACTAN | 0.01-10% |
| SUNFLOWER OIL CONCENTRATE | 0.01-10% |
| DYE | 0-0.5% |
| CITRIC ACID | 0-0.5% |

Moisturizing Anti-Redness Emulsion

| | |
| --- | --- |
| AQUA (WATER) | q.s. to 100% |
| GLYCERIN | 1-15% |
| PROPANEDIOL DICAPRYLATE | 1-15% |
| DICAPRYLYL CARBONATE | 1-15% |
| GLYCERYL STEARATE CITRATE | 1-5% |
| PRESERVATIVES | 1-5% |
| CETYL ALCOHOL | 1-5% |
| ACRYLATES/C10-30 ALKYL ACRYLATE CROSSPOLYMER | 0-2% |
| GLYCERYL CAPRYLATE | 0-2% |
| SODIUM STEAROYL GLUTAMATE | 0-2% |
| TOCOPHERYL ACETATE | 0-2% |
| SODIUM HYDROXIDE | 0-2% |
| QUINOA PEPTIDE EXTRACT | 0.01-10% |
| CYCLOCERAMIDES | 0.01-10% |
| LUPIN PEPTIDES | 0.01-10% |
| ARABINOGALACTAN | 0.01-10% |
| SUNFLOWER OIL CONCENTRATE | 0.01-10% |
| BISABOLOL | 0-2% |

Sensitive Skin Cleansing Water

| Brand or INCI name | % |
| --- | --- |
| CAPRYLOYL GLYCINE | 0-1% |
| SODA LYE | 0-1% |
| SEQUESTRANT | 0-1% |
| BUTYLENE GLYCOL | 1-5% |
| BETA CAROTENE | 0-2% |
| CYCLOCERAMIDES | 0.01-10% |
| ARABINOGALACTAN | 0.01-10% |
| PRESERVATIVES | 0-1% |
| PEG-32 | 1-5% |
| PEG-7 PALMCOCOATE | 1-5% |
| ZINC GLUCONATE | 0-1% |
| CITRIC ACID | 0-1% |
| PURIFIED WATER | q.s. to 100% |
| FRAGRANCE | 0-1% |
| POLOXAMER 184 | 1-5% |

Anti-Aging Emulsion

| Brand or INCI name | % |
| --- | --- |
| LIQUID ISOPARAFFIN | 5-20% |
| ISOCETYL STEARATE | 5-20% |
| AL-MG HYDROXYSTEARATE | 5-20% |
| ABIL WE 09 | 1-5% |
| GLYCEROL | 1-5% |
| VASELINE OIL | 1-5% |
| MICRONIZED ZINC OXIDE | 1-5% |
| BUTYLENE GLYCOL | 1-5% |
| RETINOL | 0-1% |
| VITAMIN C | 0-5% |
| ARABINOGALACTAN | 0.01-10% |
| LUPIN PEPTIDES | 0.01-10% |
| MACA PEPTIDES | 0.01-10% |
| ISONONYL ISONONANOATE | 1-5% |
| BEESWAX | 1-5% |
| SODIUM TARTRATE | 1-5% |
| SODIUM CHLORIDE | 0-5% |
| GLYCINE | 1-5% |
| PRESERVATIVES | 0-1% |
| CHOLESTEROL | 0-1% |
| PHYTOSPHINGOSINE | 0-1% |
| TARTARIC ACID | 0-1% |
| PURIFIED WATER | q.s. to 100% |

Repairing Emulsion

| Raw material/Brand or INCI name | % |
|---|---|
| HYDROGENATED POLYDECENE | 5-20% |
| LAURYLGLUCOSIDE-GLYSTEARATE | 1-5% |
| DICAPRYLYL CARBONATE | 1-5% |
| GLYCEROL | 5-20% |
| CARBOPOL | 0-1% |
| XANTHAN GUM | 0-1% |
| ASIATIC ACID | 0-1% |
| VITAMIN B5 | 0-5% |
| ARABINOGALACTAN | 0.01-10% |
| QUINOA PEPTIDE EXTRACT | 0.01-10% |
| SODA LYE | 0-1% |
| PRESERVATIVES | 0-1% |
| CITRIC ACID | 0-1% |
| PURIFIED WATER | q.s. to 100% |

Milk for Dry, Atopic Skin

| Raw material/Brand or INCI name | % |
|---|---|
| SWEET ALMOND OIL | 1-5% |
| CORN OIL | 1-5% |
| STEARIC ACID | 1-5% |
| C16-C18 CETYL ACID | 0-1% |
| ANTIFOAM 70414 | 0-1% |
| LAURIC ALCOHOL 11OE | 1-5% |
| PEG 300 MONOLAURATE | 0-1% |
| GLYCEROL MONOLEATE | 0-1% |
| GLYCEROL MONOSTEARATE | 1-5% |
| VITAMIN B12 | 0-5% |
| ARABINOGALACTAN | 0.1-10% |
| SUNFLOWER OIL CONCENTRATE | 0.01-10% |
| LUPIN PEPTIDES | 0.01-10% |
| PRESERVATIVES | 0-1% |
| CITRIC ACID | 0-1% |
| TRISODIUM CITRATE | 0-1% |
| PURIFIED WATER | qsp 100% |
| FRAGRANCE | 0-1% |
| PEANUT OIL | 1-5% |
| HYDROGENATED PALM OIL | 1-5% |

SPF 50+Sun Spray

| Raw material/Brand or INCI name | % |
|---|---|
| GLYCEROL CAPRYLOCAPRATE | 5-20% |
| CYCLOPENTASILOXANE | 10-20% |
| DICAPRYLYL CARBONATE | 5-20% |
| TINOSORB S | 1-10% |
| TITANIUM OXIDE 100 | 10-20% |
| HECTORITE | 0-5% |
| ALPHA-TOCOPHEROL | 0-2% |
| LAURYLGLUCOSIDE-GLYSTEARATE | 0-10% |
| B4 PURIFIED WATER | q.s. to 100% |
| CITRIC ACID | 0-2% |
| PENTYLENE GLYCOL | 0-5% |
| GLYCEROL | 0-5% |
| XANTHAN GUM | 0-2% |
| ARABINOGALACTAN | 0.01-10% |
| *ALOE VERA* | 0-1% |
| ZINC GLUCONATE | 0-1% |
| PRESERVATIVES | 0-2% |
| TINOSORB M | 1-10% |

5. Examples of Formulations of Compositions for Oral Administration

Arabinogalactan and lupin peptides are integrated in oral compositions, in compositions enabling the administration of 50 to 200 mg per day.

1/Anti-redness Composition in the Form of Soft Capsules

| ARABINOGALACTAN | 30 mg |
|---|---|
| LUPIN PEPTIDES | 30 mg |
| Awara oil | 60 mg |
| Unsaponifiable-rich rapeseed oil | 300 mg |
| Vitamin of group B (B1, B2, B3, B5, B6, B9, B12) | q.s. to 100% RDA |
| Tocotrienols | q.s. to 50% RDA |
| Vitamin E | |
| Beeswax | |
| Soya lecithin | |
| Alimentary gelatin | |
| Glycerin | q.s. to 1 soft capsule |

This composition is administered as four to six 500 mg capsules per day.

2/Example of Soothing Powder Stick

| ARABINOGALACTAN | 100 mg |
|---|---|
| LUPIN PEPTIDES | 100 mg |
| Polyphenol-rich tea extract | 100 mg |
| OPC-rich grape extract | 50 mg |
| Plant beta-glucans | 100 mg |
| Xanthan gum | 1 mg |
| Sodium ascorbate | 0.3 mg |
| Maltodextrin | q.s. to 5 g |

This composition is administered twice per day.

REFERENCES

[1] Yamasaki K and Gallo R L. The molecular pathology of rosacea. 2009, *J Dermatol Science;* 55:77-81.

[2] Koczulla R, von Degenfeld G, Kupatt C, Krotz F, Zahler S, Gloe T et al. An angiogenic role for the human peptide antibiotic LL37/hCAP-18. 2003, *J Clin Invest;* 111:1665-72.

[3] Rodriguez-Martinez S, Cancino-Diaz L J, Vargas-Zuniga L M, Cancino-Diaz M E. LL37 regulates the overexpression of vascular endothelial growth factor (VEGF) and c-IAP-2 in human keratinocytes. 2008, Inter Dermatol; 47:457-62.

[4] Yamasaki K, Schauber J, Coda A, Lin H, Dorschner R A, Schechter N M et al. Kallikrein-mediated proteolysis regulates the antimicrobial effects of cathelicidins in skin. 2006, FASEB J; 20:2068-80.

[5] Yamasaki K, Di Nardo A, Bardan A, Murakami M, Ohtake T, Coda A et al. Increased serine protease activity and cathelicidin promotes skin inflammation in rosacea. 2007, Nat Med; 13:975-80.

[6] Yamasaki K, Kanada K, Macleod D T, Borkowski A W, Morizane S, Nakatsuji et al. TLR2 expression is increased in rosacea and stimulates enhanced serine protease production by keratinocytes. 2011, J Invest Dermatol; 131:688-697

[7] Bevins C L and Liu T F. Rosacea: skin innate immunity gone away, 2007, Nat Med; 13:904-906

[8] Guzman-Sanchez Da, Ishiuji Y, Patel T, Fountain J, Chan Y H, Yosipovitch G. Enhanced skin blood flow and sensitivity to noxious heat stimuli in papulopustular rosacea. 2007, J Am Acad Dermatol;

[9] Laquer V, Hoang V, Nguyen A, Kelly K M. Angiogenesis in cutaneous disease: Part II. 2009, J Am Acad Dermatol; 61:945-58.

[10] Stetler-Stevenson W G. Matrix metalloproteinases in angiogenesis: a moving target for therapeutic interventions. 1999, J Clin Invest; 103:1237-41

[11] Gomaa A H, Yaar M, Eyada M M, Bhawan J. Lymphangiogenesis and angiogenesis in non-phymatous rosacea. 2007, J Cutan Pathol; 34:748-53.

[12] Smith J R, Lanier V B, Braziel R M, Falkenhagen K M, White C, Rosenbaum J T. Expression of vascular endothelial growth factor and its receptors in rosacea. 2007, Br J Ophthalmol; 91:226-229.

[13] Tokumaru S, Sayama K, Shirakata Y, Komatsuzawa H, Ouhara K, Hanakawa Y et al. Induction of keratinocyte migration via transactivation of the epidermal growth factor receptor by the antimicrobial peptide LL37. 2005, J Immunol; 175:4662-8.

The invention claimed is:

1. A method for treating a skin redness due to vascular disorders, comprising administering a cosmetic composition comprising an effective amount of a synergistic combination of arabinogalactan and lupin peptides to a person having redness, wherein the arabinogalactan is in a concentration between 0.01% and 10% by weight and the lupin peptides are in a concentration of between 0.01% and 10% by weight in the composition.

2. The method of claim 1, wherein said composition is administered topically.

3. The method of claim 1, wherein said composition is administered orally.

4. The method of claim 1, wherein the arabinogalactan is extracted from larch.

5. The method of claim 1, wherein said composition includes at least one other anti-redness agent selected from the group consisting of: permethol, genistein, esculoside, dextran sulfate, hesperidin methyl chalcone, retinoids, licochalcone, oxymetazoline, kinetin, licorice extract, vitamin P-like, butcher's broom extract, *Sophora japonica*, *Hamamelis* extract, *Ruscus*, antibiotics, polyphenols including tannins, phenolic acids, anthocyans, procyanidols, flavonoids, extracts of green tea, red berries, cocoa, grape, *Passiflora incarnata*, and *Citrus*.

6. The method of claim 1, wherein said composition comprises 0.2% of arabinogalactan.

7. The method of claim 1, wherein said composition comprises 0.2% of lupin peptides.

8. The method of claim 1, wherein said skin redness is due to an outbreak of redness on the skin.

9. A method for treating rosacea comprising administering an oral or topical composition comprising an effective amount of a synergistic combination of arabinogalactan and lupin peptides, wherein the arabinogalactan is in a concentration between 0.01% and 10% by weight and the lupin peptides are in a concentration of between 0.01% and 10% in the composition.

* * * * *

UNITED STATES PATENT AND TRADEMARK OFFICE
CERTIFICATE OF CORRECTION

PATENT NO. : 8,877,261 B2
APPLICATION NO. : 13/824699
DATED : November 4, 2014
INVENTOR(S) : Philippe Msika et al.

It is certified that error appears in the above-identified patent and that said Letters Patent is hereby corrected as shown below:

IN THE CLAIMS

Column 22, Claim 6, line 12, please replace "0.2% of arabinogalactan" with -- 2% of arabinogalactan --.

Signed and Sealed this
Twelfth Day of January, 2016

Michelle K. Lee
*Director of the United States Patent and Trademark Office*